United States Patent [19]

Johansson et al.

[11] Patent Number: 4,798,833
[45] Date of Patent: Jan. 17, 1989

[54] GUANINE DERIVATIVE

[75] Inventors: Karl N. Johansson, Enhörna; Björn G. Lindborg, Södertälje; Jan-Olof Norén, Grödinge, all of Sweden

[73] Assignee: Astra Lakemedel Aktiebolag, Sweden

[21] Appl. No.: 15,481

[22] Filed: Feb. 6, 1987

Related U.S. Application Data

[63] Continuation of Ser. No. 681,313, Dec. 13, 1984, abandoned.

[30] Foreign Application Priority Data

Dec. 20, 1983 [SE] Sweden .................. 8307051
Dec. 20, 1983 [SE] Sweden .................. 8307052

[51] Int. Cl.$^4$ ............... C07D 473/18; A61K 31/52
[52] U.S. Cl. ................. 514/262; 544/276; 544/277
[58] Field of Search ............. 544/276, 277; 514/262

[56] References Cited

U.S. PATENT DOCUMENTS 4,355,032  10/1982  Verbeyden .................. 424/253
4,495,190  1/1985  Hagberg et al. ............. 544/277

FOREIGN PATENT DOCUMENTS 2122197A  1/1984  United Kingdom .
2122198A  1/1984  United Kingdom .

OTHER PUBLICATIONS

Pandit et al., Synthetic Communications, 2(6), 345–351, 1972.
Biochemical Pharmacology, vol. 30, No. 22, pp. 3071–3077 (1981).

Primary Examiner—Nicholas S. Rizzo
Attorney, Agent, or Firm—Brumbaugh, Graves, Donohue & Raymond

[57] ABSTRACT

Antivirally active compounds of the formula

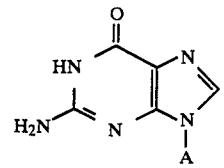

I wherein
A is

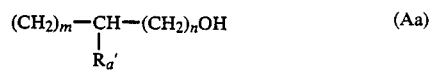
(Aa)

or

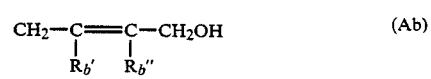
(Ab)

wherein
m is 1 or 2,
n is 1 or 2, whereby m is 1 when n is 2 and m is 2 when n is 1,
$R_a'$ is $(CH_2)_pOH$, $NHCONH_2$ or $COR_a''$,
$R_a''$ is hydrogen, hydroxy or amino,
p is 1 to 4,
$R_b'$ and $R_b''$ are independently selected from hydrogen or $(CH_2)_pOH$,
with the proviso that at least one of $R_b'$ or $R_b''$ is hydrogen; or
$R_b'$ and $R_b''$ together constitute an additional carbon-carbon bond to form an alkyne; or a physiologically acceptable salt, geometric or optical isomer thereof; pharmaceutical preparations containing the compounds and methods for treatment of virus infections.

3 Claims, No Drawings

GUANINE DERIVATIVE

This application is a continuation of application Ser. No. 681,313, filed on Dec. 13, 1984 now abandoned.

FIELD OF THE INVENTION

The present invention relates to novel deviations of guanine, methods for their preparation, novel pharmaceutical compositions and to a method for selectively combating viruses, such as herpes viruses, etc., which can cause various diseases in animals including man. such diseases include both common infections and neoplastic diseases, i.e. cancer.

BACKGROUND OF THE INVENTION

The effects of viruses on bodily functions is the end result of changes occurring at the cellular and subcellular levels. The pathogenic changes at the cellular level are different for different combinations of viruses and host cells. While some viruses cause a general destruction (killing) of certain cells, other may transform cells to a neoplastic state.

Important common viral infections are *Herpes dermatitis* (including *Herpes labialis*), *Herpes keratitis*, *Herpes genitalis*, *Herpes zoster*, *Herpes encephalitis*, infectious mononucleosis and cytomegalovirus infections all of which are caused by viruses belonging to the herpesvirus group. Other important viral diseases are influenza A and B which are caused by influenza A and B virus respectively. Another important common viral disease is viral hepatitis and especially hepatitis B virus infections are widely spread. Effective and selective antiviral agents are needed for the treatment of these diseases as well as for other diseases caused by viruses.

Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leukemias, sarcomas, breast carbinomas, Burkitt lymphomas, nasopharyngeal carcinomas and cervical cancers where RNA tumor viruses and herpes viruses are indicated. This makes the search for selective inhibitors of tumorgenic viruses and their functions an important undertaking in the efforts to treat cancer.

PRIOR ART

By the following references are guanine derivatives previously described Synthetic Communications 2 (6), 345-351 (1972), U.S. Pat. No. 4,199,574, U.S. Pat. No. 4,355,032, European patent application No. 82401571.3 (publication number 74 306) and the European patent application No. 81850250.2 (publication number 55239); the latter discloses antiviral compounds of the formula

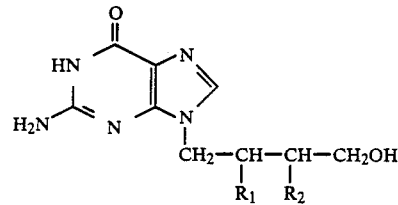

wherein $R_1$ and $R_2$ might be selected from hydrogen, hydroxy and fluoro.

DISCLOSURE OF INVENTION

The present invention relates to the novel compounds of the formula

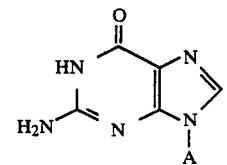   I wherein
A is

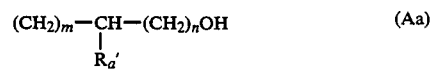   (Aa)

or

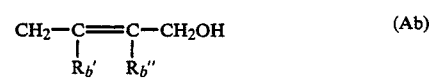   (Ab)

wherein
m is 1 or 2,
n is 1 or 2, whereby m is 1 when n is 2 and m is 2 when n is 1,
$R_a'$ is $(CH_2)_pOH$, $NHCONH_2$ or $COR_a''$,
$R_a''$ is hydrogen, hydroxy or amino,
p is 1 to 4,
$R_b'$ and $R_b''$ are independently selected from hydrogen or $(CH_2)_pOH$, with the proviso that at least one of $R_b'$ or $R_b''$ is hydrogen; or $R_b'$ and $R_b''$ together constitute an additional carbon-carbon bond to form an alkyne; with the additional proviso that when m is 2 and n is 1 and $R_a'$ is $(CH_2)_pOH$ then p is 2 to 4; or a physiologically acceptable salt, geometric or optical isomer thereof.

The invention also relates to a novel method for combating virus infections in animals and man, compounds for use at such treatment and novel pharmaceutical preparations containing a compound of the formula I, whereby when A is Aa, also $R_a'$ is $CH_2OH$ is included in the formula I, as an active ingredient within the antiviral area. Said compound is described in the prior art as a chemical compound.

It has not been found that the compounds of the invention exert an antiviral effect and inhibit certain viral vunctions including tumorgenic functions and the multiplication of viruses.

It has also been found that the compounds of the invention have especially high affinity to viral thymidine kinase, which is very important for antiviral activity when the compounds are used in cells with a high level of thymidine.

The invention thus provides compounds, geometric isomers and physiologically acceptable salts thereof, which compounds are useful in therapeutic and/or prophylactic treatment of viral diseases and which may be useful in therapeutic and/or prophylactic treatment of cancer caused by viruses.

An effective selective antiviral agent with acceptable side effects should have a selective inhibiting effect on a specific viral function of the virus to be combated. It is, therefore, one object of the present invention to provide a novel method for combating virus infections using an antiviral agent which exerts a selective inhibiting effect on viral functions but which exerts only a negligible inhibiting effect on functions of the host cells.

An especially important area of use for the compounds of the present invention is the treatment of herpesvirus infections. Among the herpesviruses may be mentioned *Herpes simplex* type 1 and 2, varicella (*Herpes zoster*), virus causing infectious mononucleosis (i.e. Epstein-Barr virus) and cytomegalovirus. Important diseases caused by herpesviruses are *herpes dermatitis* (including *herpes labialis*), *herpes genitalis, herpes keratitis, herpes encephalitis* and *herpes zoster*.

Another possible area of use for the compounds of the present invention is in the treatment of cancer and tumors, particularly those caused by viruses. This effect may be obtained in different ways, i.e. by inhibiting the transformation of virus-infected cells to a neoplastic state, by inhibiting the spread of viruses from transformed cells to other normal cells and by arresting the growth of virustransformed cells.

A further area of use for the compounds of the present invention is in the inhibition of transformed cells due to the presence in these cells of specific herpesvirus enzymes like thymidine kinase.

Possible areas of use for the compounds of the present invention with respect to cancer chemotherapy are treatment of leukemias, lymphomas including Burkitt lymphomas and Hodgkin's disease, sarcomas, breast carcinoma, nasopharyngeal carcinomas and cervical cancers in which viruses are indicated. Other possible areas of use for the compounds of the present invention with respect to cancer chemotherapy are treatment of multiple myeloma and cancer of the lungs (and bronchus), the stomach, the liver, the colon, the bladder, the lips, the bones, the kidneys, the ovary, the prostate, the pancreas, the skin (melanoma), the rectum, the salivary glands, the mouth, the esophagus, the testis, the brain (and cranial meninges), the thyroid gland, the gallbladder (and ducts), the nose, the larynx, connective tissues, the penis, the vulvas, the vagina, the corpus uteri and the tongue.

The invention furthermore provides

A. A method for the treatment of diseases caused by viruses in animals including man, comprising administering to an animal so infected a therapeutically effective amount of a compound of the formula I or a physiologically acceptable salt thereof.

B. A method for inhibiting the multiplication of virus, in particular herpesviruses, in animals including man, by administering to an animal in need of such treatment a compound of the formula I or a physiologically acceptable salt thereof in an amount sufficient for inhibiting said multiplication.

C. A method for the treatment of virus-induced neoplastic diseases in animals including man, by inhibiting the growth of cells expressing viral functions, characterized by administering to an animal so infected a therapeutically effective amount of a compound of the formula I or a physiologically acceptable salt thereof.

D. A method for inhibiting the growth of virus-transformed cells in animals including man, characterized by administering to an animal in need of such treatment a compound of the formula I or a physiologically acceptable salt thereof in an amount sufficient for inhibiting said growth.

E. A method for the treatment of virus-induced neoplastic diseases in animals including man, by inhibiting the multiplication of tumor viruses, characterized by administering to an animal in need of such treatment a compound of the formula I or a physiologically acceptable salt thereof in an amount sufficient for inhibiting such multiplication.

F. A method for the treatment of neoplastic diseases in animals including man, characterized by administering to an animal a therapeutically effective amount of a compound of the formula I or a physiologically acceptable salt thereof.

The invention also relates to the use of a compound of the formula I including the compound, wherein $R_a'$ is $CH_2OH$ when m is 2 and n is 1 or a physiologically acceptable salt thereof, in each of the above given methods A, B, C, D, E and F.

As stated previously the novel compounds of the present invention have either the formula

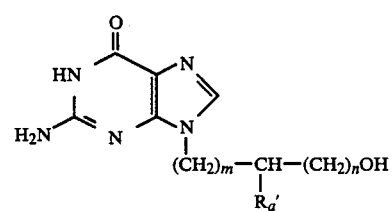

II wherein m is 1 or 2 and n is 1 or 2, whereby m is 1 when n is 2 and m is 2 when n is 1, $R_a'$ is $(CH_2)_pOH$, $NHCONH_2$ or $COR_a''$, wherein $R_a''$ is hydrogen, hydroxy or amino and where p is 1 or 4 with the additional proviso that when m is 2 and n is 1 and $R_a'$ is $(CH_2)_pOH$ then p is 2 to 4; or a physiologically acceptable salt or optical isomer thereof; or the formula

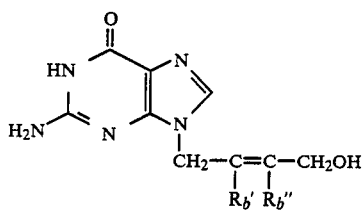

III wherein $R_b'$ and $R_b''$ are independently selected from hydrogen or $(CH_2)_pOH$, where p is 1 to 4, with the proviso that at least one of $R_b'$ and $R_b''$ is hydrogen, or $R_b'$ and $R_b''$ together constitute an additional carbon-carbon bond to form an alkyne; or a physiologically acceptable salt or geometric isomer thereof.

The proviso in the definition for m, n and $R_a'$ above mean that the following specific compounds, including salts and optical isomers thereof, constitute part of the present invention:

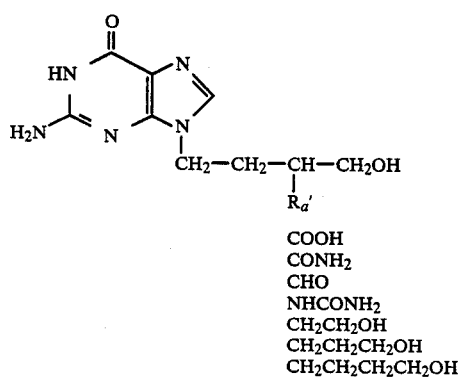

COOH
CONH$_2$
CHO
NHCONH$_2$
CH$_2$CH$_2$OH
CH$_2$CH$_2$CH$_2$OH
CH$_2$CH$_2$CH$_2$CH$_2$OH

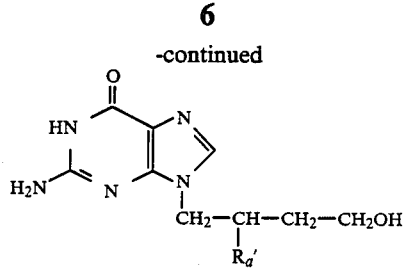

COOH
CONH$_2$
CHO
NHCONH$_2$
CH$_2$OH
CH$_2$CH$_2$OH
CH$_2$CH$_2$CH$_2$OH
CH$_2$CH$_2$CH$_2$CH$_2$OH

The compounds of the formula II contain one asymmetric center when $R_a'$ and $(CH_2)_nOH$ are different. Accordingly, they exist in two optical forms, which constitute a further aspect of the invention.

The following specific compounds, including salts and geometric isomers thereof, constitute a further part of the present invention:

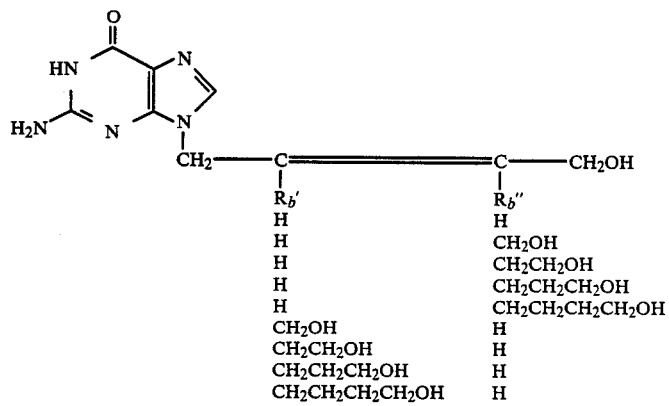

| $R_b'$ | $R_b''$ |
|---|---|
| H | H |
| H | CH$_2$OH |
| H | CH$_2$CH$_2$OH |
| H | CH$_2$CH$_2$CH$_2$OH |
| H | CH$_2$CH$_2$CH$_2$CH$_2$OH |
| CH$_2$OH | H |
| CH$_2$CH$_2$OH | H |
| CH$_2$CH$_2$CH$_2$OH | H |
| CH$_2$CH$_2$CH$_2$CH$_2$OH | H |

When $R_b''$ is not CH$_2$OH, the compound exists as two geometric isomers, which constitutes a further aspect of the invention.

The present invention comprises the following compounds;
9-[4-hydroxy-2-(hydroxymethyl)butyl]guanine,
9-[4-hydroxy-3-carboxybutyl]guanine,
9-[4-hydroxy-3-carbamoylbutyl]guanine,
9-[4-hydroxy-3-formylbutyl]guanine,
9-[4-hydroxy-3-ureidobutyl]guanine,
9-[5-hydroxy-3-(hydroxymethyl)pentyl]guanine,
9-[6-hydroxy-3-(hydroxymethyl)hexyl]guanine,
9-[4-hydroxy-2-carboxybutyl]guanine,
9-[4-hydroxy-2-carbamoylbutyl]guanine,
9-[4-hydroxy-2-formylbutyl]guanine,
9-[4-hydroxy-2-ureidobutyl]guanine,
9-[4-hydroxy-2-(hydroxyethyl)butyl]guanine,
9-[5-hydroxy-2-(hydroxyethyl)pentyl]guanine,
9-[6-hydroxy-2-(hydroxyethyl)hexyl]guanine,
9-[4-hydroxy-3-(hydroxymethyl)-2-butenyl]guanine,
9-(4-hydroxy-2-butenyl)guanine,
cis-9-(4-hydroxy-2-butenyl)guanine,
9-(4-hydroxy-2-butynyl)guanine.

A preferred sub-group of compounds of the invention is obtained when $R_a'$ is $(CH_2)_pOH$ such as hydroxymethyl or hydroxyethyl.

Further preferred compounds of the invention are 9-[4-hydroxy-3-(hydroxymethyl)-2-butenyl]guanine and cis-9-(4-hydroxy-2-butenyl)guanine.

The compound of formula III, wherein $R_b'$ and $R_b''$ form a bond has antiviral activity and said compound may also act as an intermediate for compounds of formula III, wherein $R_b'$ and $R_b''$ are hydrogen atoms.

METHODS OF PREPARATION

The compounds of the invention may be obtained by one of the following methods A-N constituting a further aspect of the invention.

A. Condensing an acyclic side chain, where the functional groups may optionally be protected, to the N-9 position of the guanine deerivative, followed by removal of the protecting groups, through one or more chemical reactions.

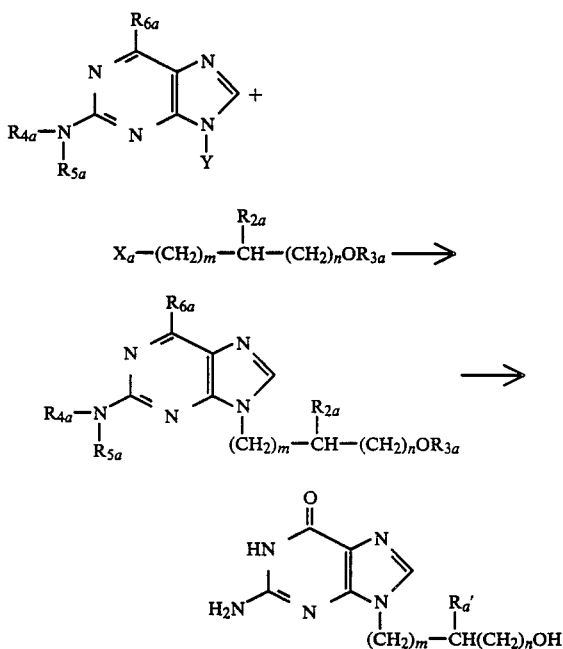

wherein m, n and $R_a'$ are as defined above in the formula I. $X_a$ and Y are generally selected from groups being able to react with each other for the formation of an optionally protected compound of the formula I. $X_a$ is e.g. a group such as chloro, bromo, iodo, or a group $OSO_2R_{7a}$ where $R_{7a}$ is alkyl containing 1-8 carbon atoms, fluorinted alkyl containing 1-8 carbon atoms such as trifluoromethyl, arylalkyl such as benzyl, or aryl. Y is e.g. hydrogen or a quaternary ammonium ion such as tetrabutylammonium. $R_{3a}$ is hydrogen or a protecting group of which a great vareity is known to those skilled in in the art (see for example "protective Groups in Organic Chemistry", T. W. Greene, Wiley 1981; "Methoden der Organischen Chemie", Houben-Weyl VI/Ib; and "Comprehensive Organic Chemistry", D. H. R. Barton and W. D. Ollis eds., 1979, Vol 1. p. 623-629).

Some examples of $R_{3a}$ are acyl groups such as acetyl or benzoyl, alkoxycarbonyl or aryloxycarbonyl groups, silyl groups such as for example tert.-butyldimethylsilyl, arylalkyl such as benzyl and triarylmethyl, or $SO_2R_{7a}$ where $R_{7a}$ is as defined above.

$R_{2a}$ is $R_a'$ as defined above in formula I, or may be CN, $COOR_{8a}$, $CH(OR_{9a})_2$, $CH(SR_{9a})_2$, $NHCONHR_{9a}$ or $(CH_2)_pOR_{9a}$, where p is as defined above, $R_{8a}$ is substituted silyl or as defined above for $R_{7a}$ and $R_{9a}$ is as defined above for $R_{3a}$, or $R_{8a}$ and $R_{9a}$ may additionally together with $R_{3a}$ form a divalent group, that is a cyclic derivative such as for example a lactone or another cyclic ester, orthoacid, acetal, ether or silyl type compound.

$R_{6a}$ is hydroxy, chloro, bromo, iodo, mercapto, alkylthio containing 1-8 carbon atoms, $SO_2R_{7a}$ as defined or an oxygen derivative $OR_{10a}$ where $R_{10a}$ is alkyl, arylalkyl such as benzyl, substituted silyl, phosphoryl diester, phosphinothioyl or $SO_2R_{7a}$ where $R_{7a}$ is as defined. $R_{4a}$ and $R_{5a}$ are the same or different and are $R_{3a}$ as defined.

The condensation is preferably conducted in an organic solvent such as for example dimethylformamide, ethanol, acetonitrile or dichloromethane, at a temperature of between 0° C. and 100° C. for 1 hour to 3 days in the presence of a base (when Y is H) such as for example potassium carbonate.

After condensation, the compounds are hydrolyzed at 0°-100° C. for 1-24 hours with acid or base such as for example acetic acid, hydrochloric acid (1-35%) in water, sodium hydroxide (1-20%) in water, ammonia (1-25%) in water or methanol, or hydrogenated with hydrogen gas in an organic solvent such as for example ethanol or dimethylformamide over a metal catalyst for 1-24 hours at a pressure of 100 to 5000 kPa (1-50 atmospheres). When $R_{2a}$ is $CH(SR_{9a})_2$, the hydrolysis may be performed with a reagent such as mercuric chloride in a separate step.

B. Condensing an unsaturated side chain, where the functional groups may optionally be protected, to the N-9 position of a guanine derivative with base catalysis, followed by reduction and/or removal of protecting groups

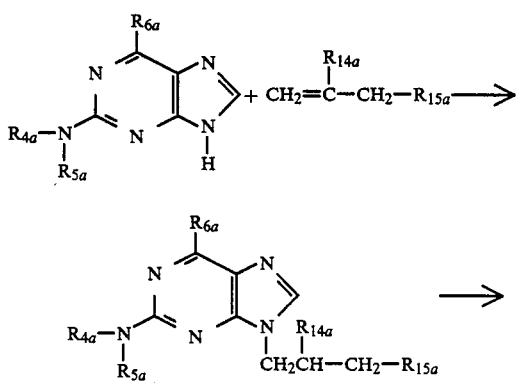

-continued

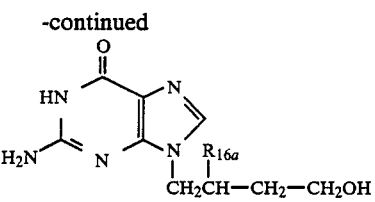

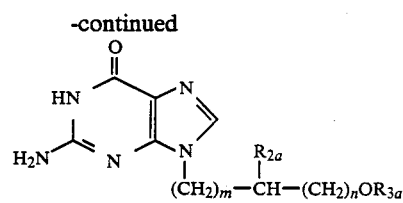

$R_{4a}$, $R_{5a}$ and $R_{6a}$ are as defined above, $R_{14a}$ is CN, CONH$_2$ or COOR$_{8a}$ and $R_{15a}$ is COOR$_{8a}$ or CH$_2$OR$_{9a}$, where $R_{8a}$ and $R_{9a}$ are as defined above and may additionally together form a divalent group, that is a cyclic derivative such as for example a lactone or another cyclic ester, orthoacid, acetal, ether or silyl type compound, and $R_{16a}$ is CONH$_2$, COOH or CH$_2$OH.

The condensation is preferentially conducted in an organic solvent such ad for example dimethylformamide, ethanol, acetonitrile or dichloromethane, at a temperature of between 0° C. and 100 C. for 1 hour to 3 days in the presence of a base catalyst such as for example potassium carbonate, sodium methoxide, sodium hydride or tetrabutylammonium hydroxide.

C. Reduction or selective reduction or derivatized or activated carboxylic acid groups, followed by removal of protecting groups.

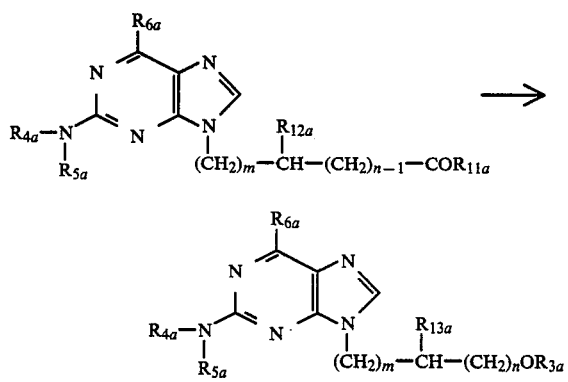

m, n, $R_{3a}$, $R_{4a}$, $R_{5a}$ and $R_{6a}$ are as defined above, $R_{11a}$ is $R_{6a}$ as defined above or a group such as (CH$_3$)$_2$N$^\oplus$=CHO— in an activated carboxylic acid derivative, $R_{12a}$ is $R_{2a}$ or a group (CH$_2$)$_{p-1}$COR$_{11a}$, where $R_{2a}$, $R_{11a}$ and p are as defined above and $R_{13a}$ is $R_a'$ or $R_{12a}$ as defined above.

The reduction may be performed by hydrogen gas or hydrogen generated in situ, with a metal as catalyst or, preferentially, a hydrid reducing agent in an organic solvent.

D. Pyrimidine ring closure to the guanine base of a substituted imidazole derivative

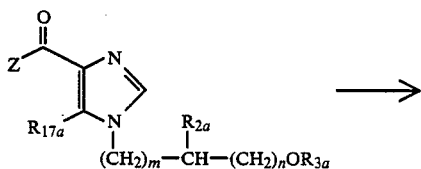

wherein m, n, $R_{2a}$ and $R_{3a}$ are as defined above, Z is NH$_2$ or alkoxy i.e. COZ is an amide or ester group and $R_{17a}$ is NH$_2$ or guanidino. The ring closure may be performed by known methods (the principles of which are given for example in "Comprehensive Organic Chemistry" p. 505–508, 1979, vol. 4, D. H. R. Barton and W. D. Ollis eds.).

The ring closure is performed in an organic solvent at a temperature from 50° to 250° with or without the addition of a reagent such as for example guanidine. When $R_{2a}$ and $R_{3a}$ are not $R_a'$ and hydrogen, respectively, the side chain protecting groups are removed in a subsequent reaction step according to method A.

E. Imidazole ring closure, to the guanine base, of a substituted pyrimidine derivative

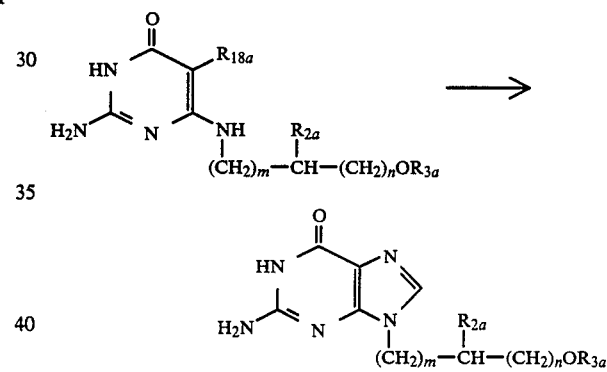

where m, n, $R_{2a}$ and $R_{3a}$ are as defined above and $R_{18a}$ is nitroso, nitro, amino, or an amino derivative such as formylamino (—NH—CHO) or ortho ester amino (e.g.

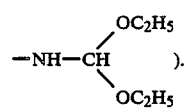

).

The ring closure may be performed by known methods (the principles of which are given for example in "Comprehensive Organic Chemistry" p. 499–504, 1979, Vol. 4, D. H. R. Barton and W. D. Ollis eds.).

The ring closure may be performed in an organic solvent such as for example formic acid, formamide, orthoformate ester at a temperature from 50° to 250° C. for ½ hour to 10 hours. When $R_{18a}$ is nitroso or nitro, these groups first have to be reduced to amino groups by known methods. When $R_{2a}$ and $R_{3a}$ are not $R_a'$ and hydrogen, respectively, the side chain protecting groups are removed in a subsequent reaction step according to method A.

F. Substitution in the pyrimidine ring of a purine for the formation of a guanine ring

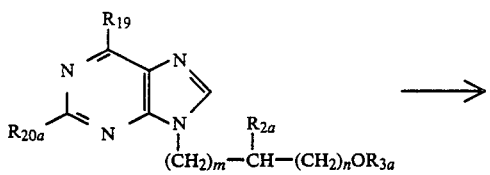

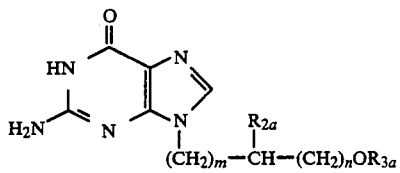

m, n, $R_{2a}$ and $R_{3a}$ are as defined above, $R_{19a}$ is chloro, bromo, iodo, hydroxy or amino and $R_{20a}$ is fluoro, chloro, bromo, iodo or amino. When $R_{20a}$ is not amino it is substituted by ammonia in an organic solvent such as methanol, from normal to higher pressure at room temperature to 100° C. for 1 to 25 hours or by an azide ion followed by hydrogenation by known methods. When $R_{19a}$ is amino it can be substituted to a hydroxyl function by selective diazotization with nitrite in a solvent such as acetic acid at a temperature from 0° C. to 50° C. for 1-24 hours and when $R_{19a}$ is a halogen atom it may additionally be hydrolyzed to hydroxyl according to method A.

G. Condensing an acyclic side chain, where the functional groups may optionally be protected, to the N-9 position of the guanine derivative, followed by removal of the protecting groups, through one or more chemical reactions.

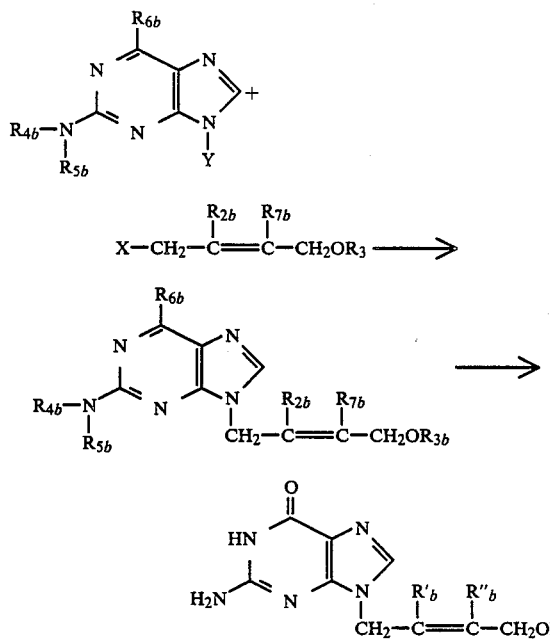

wherein $R_b'$ and $R_b''$ are as defined above in the formula I. $X_b$ and Y are generally selected from groups being able to react with each other for the formation of an optionally protected compound of the formula I. $X_b$ is e.g. a group such as chloro, bromo, iodo, or a group $OSO_2R_{8b}$ where $R_{8b}$ is alkyl containing 1-8 carbon atoms, fluorinated alkyl containing 1-8 carbon atoms such as trifluoromethyl, arylalkyl such as benzyl, or aryl. Y is e.g. hydrogen or a quaternary ammonium ion such as tetrabutylammonium. $R_{3b}$ is hydrogen or a hydroxy protecting group of which a great variety is known to those skilled in the art (see for example "Protective Groups in Organic Chemistry", T. W. Greene, Wiley 1981; "Methoden der Organischen Chemie", Houben-Weyl VI/1b; and "Comprehensive Organic Chemistry", D. H. R. Barton and W. D. Ollis eds., 1979, Vol. 1. p. 623–629).

Some examples of $R_{3b}$ are acyl groups such as acetyl or benzoyl, alkoxycarbonyl or aryloxycarbonyl groups, silyl groups such as for example tert.-butyldimethylsilyl, arylalkyl such as benzyl and triarylmethyl, or $SO_2R_{8b}$ where $R_{8b}$ is as defined above.

$R_{2b}$ is $R_b'$ and $R_{7b}$ is $R_b''$ as defined above in formula I, or both may be $(CH_2)_pOR_{9b}$, where p is 1 to 4 and $R_{9b}$ is as defined for $R_{3b}$, and $R_{9b}$ and $R_{3b}$ are the same or different and may additionally together form a divalent group, that is a cyclic derivative such as for example a carbonate ester, thiocarbonate ester or the corresponding orthoacid cyclic derivatives or cyclic acetal type compounds. $R_{6b}$ is hydroxy, chloro, bromo, iodo, mercapto, alkylthio containing 1-8 carbon atoms, $SO_2R_{8b}$ where $R_{8b}$ is as defined or an oxygen derivative $OR_{10b}$ where $R_{10b}$ is alkyl, arylalkyl such as benzyl, substituted silyl, phosphoryl diester, phosphinothioyl or $SO_2R_{8b}$ where $R_{8b}$ is as defined. $R_{5b}$ and $R_{6b}$ are the same or different and are $R_{3b}$ as defined.

The condensation is preferably conducted in an organic solvent such as for example dimethylformamide, ethanol, acetonitrile or dichloromethane, at a temperature of between 0° C. and 100° C. for 1 hour to 3 days in the presence of a base (when Y is H) such as for example potassium carbonate.

After condensation, the compounds are hydrolyzed at 0°–100° C. for 1–24 hours with acid or base such as for example acetic acid, hydrochloric acid (1–35%) in water, sodium hydroxide (1–20%) in water, ammonia (1–25%) in water or methanol.

H. Condensing an unsaturated side chain, where the functiional groups may optionally be protected, to the N-9 position of a guanine derivative with metal catalysis, followed by removal of the protecting groups, through one or more chemical reactions.

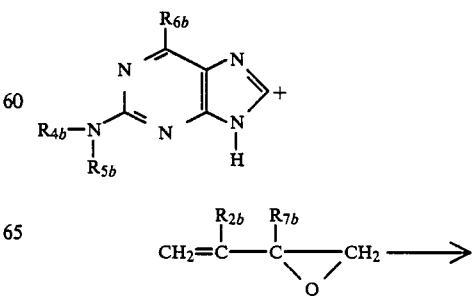

-continued

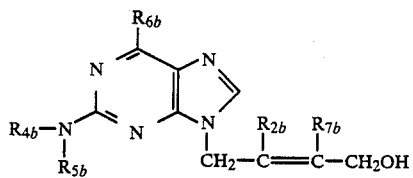

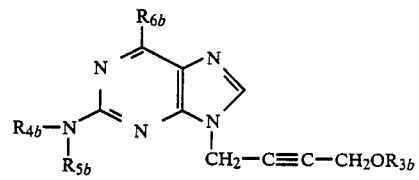

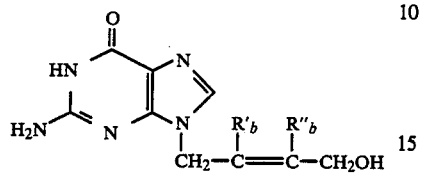

$R_b'$, $R_b''$, $R_{2b}$, $R_{4b}$, $R_{5b}$, $R_{6b}$ and $R_{7b}$ are as defined above.

The condensation is preferably conducted in an organic solvent such as for example dimethylformamide, ethanol, acetonitrile or dichloromethane, at a temperature of between 0° C. and 100° C. for 1 hour to 3 days in the presence of a metal catalyst, such as for example tetrakis(triphenylphosphine)palladium(O).

J. Reduction of derivatized or activated carboxylic acid groups to alcohol, followed by removal of protecting groups.

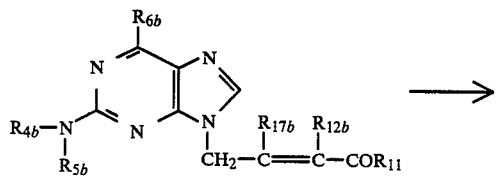

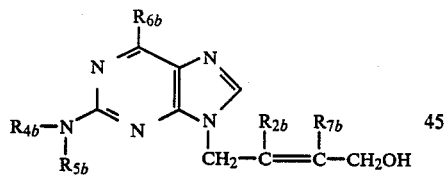

$R_{2b}$, $R_{4b}$, $R_{5b}$, $R_{6b}$ and $R_{7b}$ are as defined above. $R_{11b}$ is $R_{6b}$ as defined above or a group such as $(CH_3)_2N^{\oplus}{=}CHO{-}$ in an activated carboxylic acid derivative. $R_{12b}$ is $R^{7b}$ or $(CH_2)_{p-1} COR_{11b}$ as defined above, $R_{17b}$ is $R_{2b}$ or $(CH_2)_{p-1} COR_{11b}$ as defined above, and $R_{11b}$ and $R_{12b}$ or $R_{11b}$ and $R_{17b}$ may additionally together form a divalent group, that is a cyclic derivative such as for example a lactone or another cyclic ester, orthoacid, acetal, ether or silyl type compound.

The reduction may be performed by hydrogen gas or hydrogen generated in situ, with a metal as catalyst or, preferentially, a hydride reducing agent in an organic solvent.

K. Partial reduction of the triple bond of a compound of the formula

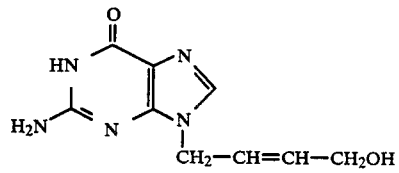

wherein $R_{3b}$, $R_{4b}$, $R_{5b}$ and $R_{6b}$ are as defined above, followed by removal of the optional protecting groups to yield

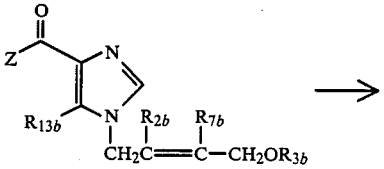

The reduction is performed according to known methods, such as for example by hydrogen gas with a metal as catalyst to yield the cis isomer, or with sodium metal dissolved in liquid ammonium to yield the trans isomer.

L. Pyrimidine ring closure to the guanine base of a substituted imidazole derivative.

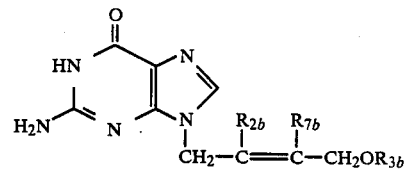

wherein $R_{2b}$, $R_{3b}$ and $R_{7b}$ are as defined above, Z is $NH_2$ or alkoxy i.e. COZ is an amide or ester group and $R_{13b}$ is $NH_2$ or guanidino. The ring closure may be performed by known methods (the principles of which are given for example in "Comprehensive Organic Chemistry" p. 505–508, 1979, vol. 4, D. H. R. Barton and W. D. Ollis eds.).

The ring closure is performed in an organic solvent at a temperature from 50° to 250° with or without the addition of a reagent such as for example guanidine. When $R_{3b}$ is not hydrogen, $R_{2b}$ is not $R_b'$ and $R_{7b}$ is not $R_b''$, the side chain protecting groups are removed in a subsequent reaction step according to method G.

M. Imidazole ring closure, to the guanine base, of a substituted pyrimidine derivative.

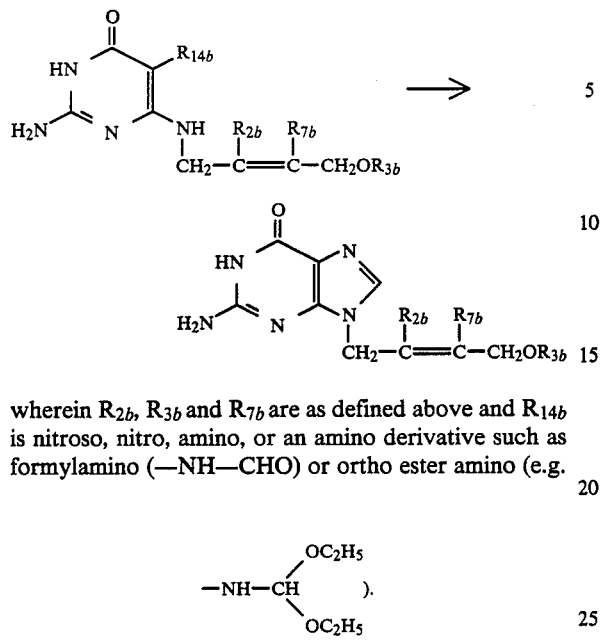

wherein $R_{2b}$, $R_{3b}$ and $R_{7b}$ are as defined above and $R_{14b}$ is nitroso, nitro, amino, or an amino derivative such as formylamino (—NH—CHO) or ortho ester amino (e.g.

$$-NH-CH\begin{array}{c}OC_2H_5\\ \\OC_2H_5\end{array}).$$

The ring closure may be performed by known methods (the principles of which are given for example in "Comprehensive Organic Chemistry" p. 499–504, 1979, Vol. 4, D. H. R. Barton and W. D. Ollis eds.).

The ring closure may be performed in an organic solvent such as for example formic acid, formamide, orthoformate ester at a temperature from 50° to 250° C. for ½ hour to 10 hours. When $R_{14b}$ is nitroso or nitro, these groups first have to be reduced to amino groups by known methods. When $R_{3b}$ is not hydrogen, $R_{2b}$ is not $R_b'$ and $R_{7b}$ is not $R_b''$, the side chain protecting groups are removed in a subsequent reaction step according to method G.

N. Substitution in the pyrimidine ring of the purine for the formation of a guanine ring.

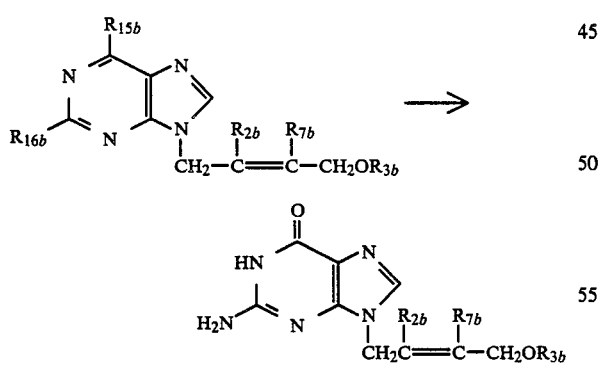

$R_{2b}$, $R_{3b}$ and $R_{7b}$ are as defined above, $R_{15b}$ is chloro, bromo, iodo, hydroxy or amino and $R_{16b}$ is fluoro, chloro, bromo, iodo, or amino. When $R_{16b}$ is not amino it is substituted by ammonia in an organic solvent such as methanol, from normal to higher pressure at room temperature to 100° C. for 1 to 25 hours or by an azide ion followed by hydrogenation by known methods. When $R_{15b}$ is amino it can be substituted to a hydroxyl function by selective diazotization with nitrite in a solvent such as acetic acid at a temperature from 0° C. to 50° C. for 1–24 hours and when $R_{15b}$ is a halogen atom it may additionally be hydrolyzed to hydroxyl according to method G.

The described methods A–F may be used to give mixtures of optical isomers, or in appropriate cases a single optical isomer. Additionally a single optical isomer may be obtained from the racemic mixtures by methods known per se.

The described method G–N may be used to give mixtures of geometric isomers, or in appropriate cases a single geometric isomer. Additionally a single geometric isomer may be obtained from the isomeric mixtures by methods known per se.

The starting materials in the above methods A–N are either known compounds or can be prepared by methods known to those skilled in the art.

These groups of new compounds can be prepared in a way known per se.

SALTS

Physiologically acceptable salts of compounds of the invention are prepared by methods known in the art. The salts are novel compounds and comprise a further aspect of the invention. Metal salts can be prepared by treating a metal hydroxide with a compound of the invention. Examples of metal salts which can be prepared in this way are salts containing Li, Na and K. A less soluble metal salt can be precipitated from a solution of a more soluble salt by addition of a suitable metal compound. Acid salts can be prepared by treating a compound of the invention with an acid such as HCl, HBr, H$_2$SO$_4$, or an organic sulphonic acid.

PHARMACEUTICAL PREPARATIONS

Pharmaceutical preparations of the compounds of the formula I

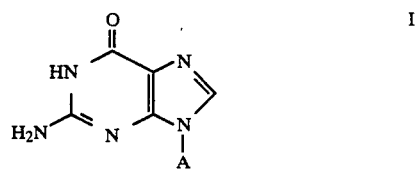

wherein
A is

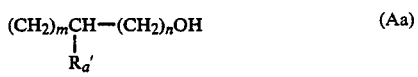 (Aa)

or

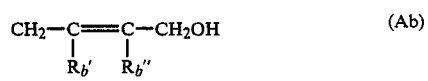 (Ab)

wherein
m is 1 or 2,
n is 1 or 2, whereby m is 1 when n is 2 and m is 2 when n is 1,
$R_a'$ is $(CH_2)_pOH$, $NHCONH_2$ or $COR_a''$,
$R_a''$ is hydrogen, hydroxy or amino, p is 1 to 4, $R_b'$ and $R_b''$ is independently selected from hydrogen or $(CH_2)_pOH$, with the proviso that at least one of $R_b'$ or $R_b''$ is hydrogen; or $R_b'$ and $R_b''$ together constitute an additional carbon-carbon bond to form an alkyne; or a physiologically acceptable salt, geometric or optical isomer thereof, with a pharmaceutically acceptable carrier, constitute a further aspect of the invention.

The compounds of the invention can be administered systemically or locally and will in clinical practice normally be administered topically, orally, intranasally, by injection, by infusion, or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. The compounds may also be used without carrier material. As examples of pharmaceutical preparations may be mentioned tablets, solutions, drops, such as nasal drops, eye drops, preparations for topical application such as ointments, jellies, creams and suspensions, aerosols for inhalation, nasal spray, liposomes, etc. Usually the active substance will comprise between 0.01 and 99, or between 0.1 and 99% by weight of the preparation, for example between 0.5 or 20% for preparations intended for injection and between 0.1 and 50% for preparations intended for oral administration.

The preparations are preferably in dosage unit form. Further, they are preferably provided in sterilized form.

To produce pharmaceutical preparations in the form of dosage unit for oral application containing a compound of the invention the active ingredient may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax® or other polyethylene glycol waxes and compressed to form tablets or cores for dragées. If dragées are required, the cores may be coated for example with concentrated sugar solutions which may contain gum arabic, talc and/or titanium dioxide, or alternatively with a film forming agent dissoled in easily volatile organic solvents or mixtures of organic solvents. Dyestuffs can be added to these coatings, for example, to distinguish between different contents of active substance. For the preparation of soft gelatine capsules consisting of gelatine and, for example, glycerol and a plasticizer, or similar closed capsules, the active substance may be admixed with a Carbowax® or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as physiologically inert plastic substance.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution of the active drug or a physiologically acceptable salt thereof, desirably in a concentration of 0.05–10%, and optionally also a stabilizing agent and/or buffer substances in aqueous solution. Dosage units of the solution may advantageously be enclosed in ampoules.

For topical application, especially for the treatment of herpesvirus infections on skin, genitals and in mouth and eyes the preparations are suitably in the form of a solution, ointment, gel, suspension, cream or the like. The amount of active substance may vary, for example between 0.05–20% by weight of the active substance. Such preparations for topical application may be prepared in known manner by mixing the active substance with known carrier materials such as isopropanol, glycerol, paraffin, stearyl alchol, polyethylene glycol, polypropylen glycol, etc. The pharmaceutically acceptable carrier may also include a known chemical absorption promoter. Examples of absorption promoters are e.g. dimethylacetamide (U.S. Pat. No. 3,472,931), trichloroethanol or trifluoroethanol (U.S. Pat. No. 3,891,757), certain alcohols and mixtures thereof (British Pat. No. 1,001,949). It may also contain detergents to facilitate the penetration of the active substance into the skin.

The dosage at which the active ingredients are administered may vary within a wide range and will depend on various factors such as for example the severity of the infection, the age of the patient, etc., and may have to be individually adjusted. As a possible range for the amount of the compounds of the invention which may be administered per day may be mentioned from about 0.1 mg to about 2000 mg, preferably from 1 mg to about 2000 mg for topical administration, from 50 mg to about 2000 mg or from 100 to about 1000 mg for oral administration and from 10 mg to about 2000 mg of from 50 to about 500 mg for injection.

In severe cases it may be necessary to increase these doses 5-fold to 10-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that the compounds of the formula I and the physiologically acceptable salts thereof can be used to inhibit herpesvirus multiplication. The compounds of the formula I and physiologically acceptable salts thereof are useful in therapeutic and/or prophylactic treatment of virus infections.

A preferred aspect of the invention is the use of a compound of the formula I including the compound, wherein $R_a'$ is $CH_2OH$ when m is 2 and n is 1; or a physiologically acceptable salt thereof, in the treatment of herpesvirus infections.

WORKING EXAMPLES

The following examples illustrate the preparation of compounds according to the invention.

EXAMPLE 1

9-[4-hydroxy-2-(hydroxymethyl)butyl]guanine
(Method C)

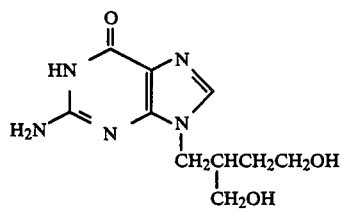

VSA 671

A suspension of sodium borohydride (135 mg, 3.57 mmol) and dried lithium bromide (220 mg, 2.53 mmol) in 4 ml of dried and distilled diglyme was stirred at room temperature for ½h. After addition of dimethyl 2-(2-amino-6-chloropurin-9-ylmethyl)succinate (215 mg, 0.656 mmol) and 3 drops of trimethyl borate the mixture was stirred at room temperature over-night and then kept at 100° C. for 5 h. The solvent was evaporated in vacuum and the residue dissolved in 10 ml of 70% formic acid in water and kept at 50° C. over-night. The mixture was evaporated to dryness in vacuum, dissolved in water, neutralized with sodium hydrogen carbonate and evaporated in vacuum. Chromatography (silica gel, ethyl acetate+methanol+water 4+3+1 parts of volume) and recrystallization from water afforded 99 mg of 9-[4-hydroxy-2-(hydroxymethyl)-butyl]guanine. The compound was purified by preparative HPLC (Porasil C$_{18}$ reversed-phase column; methanol+water 20+80) to yield a pure product after recrystallization from water. M.p. 235° C.

UV spectrum, $\lambda_{max}$ (nm): 0.01M HCl: 253 (277); H$_2$O (pH 7): 252 (270 infl.); 0.01M NaOH: 268 (256 infl.).

$^1$H NMR (DMSO-d$_6$): δ1.43 (m, 2H) CH$_2$CH$_2$OH; 2.09 (m, 1H) CH; 3.34 (d, 2H) CHCH$_2$OH; 3.47 (t, 2H) CH$_2$CH$_2$OH; 3.96 (ABX system, 2H) NCH$_2$; 6.25 (broad s, 2H) NH$_2$; 7.59 (s, 1H) H$_8$; 10.4 (broad s, 1H) NH.

The starting compound, dimethyl 2-(2-amino-6-chloropurin-9-ylmethyl)succinate was prepared as follows: (Method B)

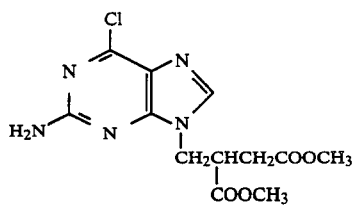

A mixture of 2-amino-6-chloropurine (4.07 g, 0.024 mol), dimethyl itaconate (5.00 g, 0.032 mol), and sodium hydride (55% in oil, 0.2 g) in 50 ml of dry dimethylformamide was stirred at room temperature for 3 days. About 50 ml of water was added and the mixture was washed with n-hexane (2×50 ml) and then extracted with 2×50 ml of dichloromethane. The combined CH$_2$Cl$_2$ extracts were washed with 2×20 ml of water, dried with magnesium sulfate, and evaporated in vacuum. Treatment with ether and drying afforded a white crystalline product. Chromatography (silica gel, chloroform+methanol 15+1) yielded 5.54 g (71%) or recrystallization (MeOH-H$_2$O) yielded 5.15 g (66.1%) of dimethyl 2-(2-amino-6-chloropurin-9-ylmethyl)succinate.

UV spectrum in EtOH, $\lambda_{max}$ (nm): 310 (247).

$^1$NMR (CDCl$_3$) δ2.67 (dd, 2H) CH$_2$COO; 3.46 (m, 1H) CH; 3.70 (2s, 2×H) OCH$_3$; 4.42 (ABX system, J$_{gem}$=14 Hz, 2H) NCH$_2$; 5.35 (broad s, 2H) NH$_2$; 7.79 (s, 1H) H$_8$.

EXAMPLE 2

9-[4-Hydroxy-3-(hydroxymethyl)butyl]guanine
(Method A)

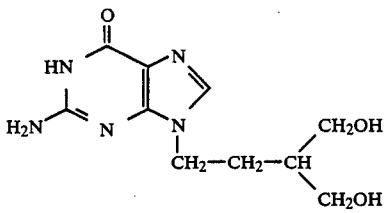

VIS 873

A mixture of 2-amino-6-chloropurine (1.275 g, 7.5 mmol) and potassium carbonate (0.69 g, 5 mmol) in dry dimethylformamide (30 ml) was sonicated for 15 min., benzyl 2-benzyloxymethyl-4-bromobutyl ether (1.82 g, 5 mmol) was added, and the mixture was sonicated for 4h and then stirred over-night. After evaporation in vacuum the residue was extracted with 3×50 ml of chloroform and the extracts were evaporated to dryness in vacuum. Chromatography (silica gel, chloroform+methanol 20+1 by volume) afforded 0.58 g (26%) of pure compound 4-(2-amino-6-chloropurin-9-yl)-2-benzyloxymethylbutyl benzyl ether. A small sample of said compound was recrystallized from toluene. M.p. 108.5°-109.5° C.

$^1$H NMR (CDCl$_3$): δ1.96 (m, 3H) N—C—CH$_2$CH; 3.48 (ABX system, 4H) (CH(CH$_2$O)$_2$; 4.13 (t, 2H)

NCH$_2$; 4.46 (s, 4H) OCH$_2$Ph; 5.49 (s, 2H) NH$_2$; 7.30 (m, 10H) phenyl; 7.69 (s, 1H) H$_8$.

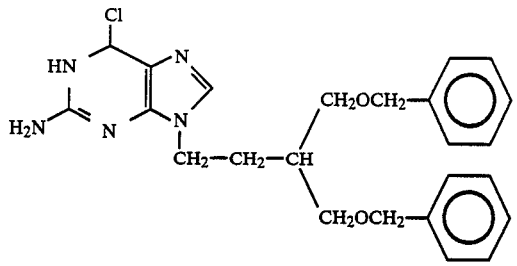

DEPROTECTION

A solution of 4-(2-amino-6-chloropurin-9-yl)-2-benzyloxymethylbutyl benzyl ether (0.904 g, 2 mmol) in 25 ml of 80% aqueous formic acid was kept at 100° C. for 1h, palladium catalyst (10% on carbon, 0.40 g) was added, and the mixture was hydrogenated at room temperature and atmospheric pressure with efficient stirring for 45 min. After evaporation in vacuum to dryness the residue was heated to boiling with 50 ml of water, 1 ml of concentrated aqueous ammonia was added, the solution was boiled gently for a short while and then evaporated to dryness. Recrystallization from water afforded 0.23 g (45%) of 9-[4-hydroxy-3-(hydroxymethyl)butyl]guanine. M.p. 252°-262° C. (decomposition, slow heating) or 264°-265° (fast immersion of the capillary).

$^1$H NMR (DMSO-d$_6$): δ1.51 (m, 1H) CH; 1.76 (q, 2H) N—C—CH$_2$; 3.42 (ABX system, 4H) 2CH$_2$O; 4.02 (t, 2H) NCH$_2$; 6.29 (broad s, 2H) NH$_2$; 7,64 (s, 1H) H$_8$; 10.3 (broad s, 1H) NH.

UV, λ$_{max}$ (nm): ethanol 255 ε12300 (~270 infl.);
1M HCl 253 ε11300, 279;
1M NaOH 268 (257 infl.).

The starting compound, benzyl 2-benzyloxymethyl-4-bromobutyl ether was prepared as follows:

(a) Diethyl (2,2-dimethoxyethyl)malonate

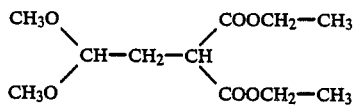

Diethyl malonate (168.18 g, 1.05 mol) was added to a solution of sodium ethoxide (from 23.0 g, 1.00 mol of sodium) in 500 ml of dry ethanol at 50° C. during 45 min. Bromoacetaldehyde dimethylacetal (74.2 g, 1.06 mol) was added at the same temperature during 45 min. and the mixture was refluxed over-night. Ethanol was evaporated in vacuum, and the residue was dissolved in 200 ml of water and extracted with 3×300 ml of ether. The extracts were dried (MgSO$_4$), evaporated, and distilled in vacuum to give 115.0 g (46%) of the title compound. B.p. 97°-101° C. (0.6 mm Hg).

$^1$H NMR (CDCl$_3$): δ1.30 (t, J=7 Hz, 6H) 2C—CH$_3$; 2.20 (dd, J=5 Hz and 7 Hz, 2H) CH—CH$_2$; 3.35 (s, 6H) 2OCH$_3$; 3.44 (t,1H) COCHCO; 4.20 (q, J=7 Hz, 4H) 2OCH$_2$; 4.42 (t, J=5 Hz, 1H) O—CH—O.

(b) 4,4-Dimethoxy-2-(hydroxymethyl)butanol

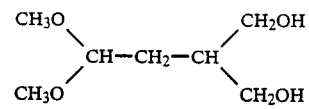

Diethyl (2,2-dimethoxyethyl)malonate (115.0 g, 0.46 mol) was added to a suspension of lithium aluminum hydride (38.0 g, 1.00 mol) in 400 ml of dry ether at a rate to maintain a gentle reflux. After stirring for 15 min. 40 ml of water, 40 ml of 15% aqueous NaOH, and 120 ml of water were added and stirring was continued until a white suspension was obtained. The inorganic salts were filtered off and extracted with several 200 ml portions of tetrahydrofuran (THF). The combined organic extracts were evaporated and distilled twice in vacuum to yield 50.23 g (66.5%) of the title compound. B.p. 116°-125° (0.02 mm Hg).

$^1$H NMR (CDCl$_3$): δ1.6-2.1 (m, 3H) CH$_2$—CH; 3.35 (s, 6H) 2OCH$_3$; 3.67 (d, 4H) 2CH$_2$O; 4.48 (t, J=5 Hz, 1H) O—CH—O.

(c) Benzyl 2-(benzyloxymethyl)-4,4-dimethoxybutyl ether

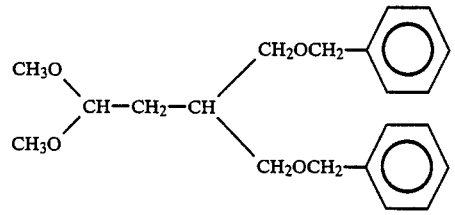

Sodium hydride (55% in oil, 32.72 g, 0.75 mol) was washed twice with n-hexane and suspended in 200 ml of THF. 4,4-Dimethoxy-2-(hydroxymethyl)butanol (49.26 g, 0.3 mol) was added dropwise to maintain a gentle evolution of hydrogen gas. Then benzyl chloride (94.94 g, 0.45 mol) was added during 30 min. and the mixture was refluxed over-night, cooled, diluted with 50 ml of ethanol, and evaporated in vacuum. The residue was suspended in about 200 ml of water and extracted with 3×100 ml of ether. The combined organic extracts were dried (MgSO$_4$) and distilled in vacuum. The title compound (94.34 g, 91%) was obtained at 197°-200° C. (0.01 mm Hg).

$^1$H NMR (CDCl$_3$): δ1.67 (diffuse t, 2H) CHCH$_2$CH; 2.02 (m, 1H) CH; 3.23 (s, 6H) 2OCH$_3$; 3.46 (d, 4H) 2CH$_2$O; 4.43 (s, 4H) 2OCH$_2$Ph; 4.43 (t, 1H) O—CH—O; 7.27 (broad s, 10H), phenyl.

(d) 4-Benzyloxy-3-benzyloxymethylbutan-1-ol

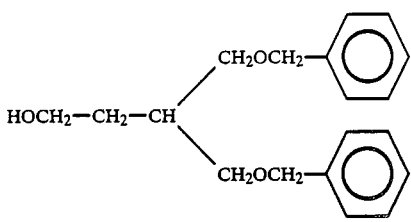

A mixture of benzyl 2-benzyloxymethyl-4,4-dimethoxybutyl ether (51.62 g, 0.15 mol), acetic acid (70 ml), water (30 ml), and THF (100 ml) was refluxed for 2 h and then evaporated in vacuum. The residue was dissolved in ether and the solution washed with aqueous potassium carbonate solution and water, dried (MgSO$_4$), and evaporated in vacuum. The residue of crude 4-benzyloxy-3-benzyloxymethylbutanal (quantitative yield) was dissolved in 100 ml of THF and added during 30 min. to a suspension of lithium aluminum hydride (7.6 g, 0.20 mol) in 100 ml of THF. Then 8 ml of water, 8 ml of 15% aqueous NaOH and 24 ml of water were added and the mixture was stirred until a white, sandy suspension was obtained. The inorganic salts were filtered off and washed with several portions of THF. The combined extracts were evaporated in vacuum to yield 41.93 g (93%) of the title compound.

$^1$H NMR (CDCl$_3$): δ1.66 (q, 2H) C$\underline{H}_2$CH$_2$O; 2.05 (m, 1H) CH; 3.0 (t, 1H) OH; 3.46 (d, 4H) CH(C$\underline{H}_2$O)$_2$; 3.64 (q, 2H) CH$_2$OH; 4.47 (s, 4H) 2 OCH$_2$Ph; 7.30 (m, 10H) phenyl.

(e) Benzyl 2-benzyloxymethyl-4-bromobutyl ether

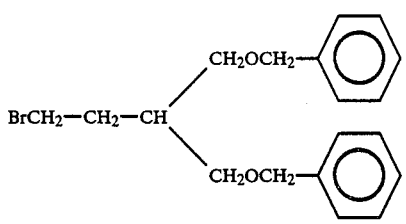

A solution of 4-benzyloxy-3-benzyloxymethylbutan-1-ol (41.75 g, 139 mmol) in 150 ml of dry dichloromethane was cooled in ice-water bath. Triphenylphosphine (42.0 g, 160 mmol) was added with stirring and then N-bromosuccinimide (26.0 g, 146 mmol) in portions during 15 min. After 1 h at room temperature ether (400 ml) was added and the precipitated triphenylphosphine oxide filtered off. The solution was concentrated in vacuum to a small volume, and more ether was added to extract the product from precipitated triphenylphosphine oxide. Finally, this extraction-precipitation step was repeated with light petroleum to give, after evaporation, 33.55 g (66%) of crude title compound.

$^1$H NMR (CDCl$_3$): δ1.98 (q, 2H) Br—C—C$\underline{H}_2$; 2.15 (m, 1H) CH; 3.45 (t, 2H) BrCH$_2$; 3.47 (m, 4H) CH(C$\underline{H}_2$O)$_2$; 4.47 (s, 4H) 2OCH$_2$Ph; 7.30 (m, 10H) phenyl.

EXAMPLE 3

9-[4-hydroxy-2-(hydroxymethyl)butyl]guanine (Method C)

VSA 671

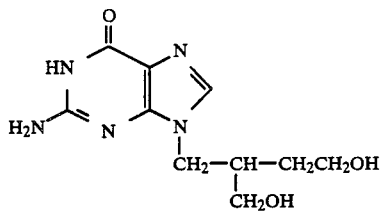

Dimethyl 2-(2-amino-6-chloropurin-9-ylmethyl)succinate (8.00 g, 0.0244 mol) was dissolved in 200 ml of tert. butanol at 50° C., lithium borohydride (2.66 g, 0.122 mol) was added in portions, and the mixture was stirred for 1 h. Then 100 ml of water was added and the stirring was continued over-night, the inorganic salts were filtered off and the solution was evaporated to dryness in vacuum. The residue was found to contain 78 mole-% of 2-amino-6-tert.butoxy-9-[4-hydroxy-2(hydroxymethyl)butyl]purine together with the 6-chloro compound.

$^1$H NMR(DMSO-d$_6$): δ1.10 (s, 9H) C(CH$_3$)$_3$; 1.38 (m, 2H) C$\underline{H}_2$CH$_2$OH; 2.14 (m, 1H) CH; 3.34 (d, 2H) CHC$\underline{H}_2$OH; 3.45 (diffuse t, 2H) CH$_2$C$\underline{H}_2$OH; 4.06 (t, ABX system, 2H) NCH$_2$; ~4.5 (very broad s) OH; 6.77 (s, 2H) NH$_2$; 8.08 (s, 1H) H8.

$^{13}$C NMR (DMSO-d$_6$): δ31.41, C(C$\underline{H}_3$)$_3$; 31.92, C$\underline{H}_2$CH$_2$OH; 37.88, CH; 45.01, NCH$_2$; 58.72 and 61.3, 2CH$_2$OH; 66.65, $\underline{C}$(CH$_3$)$_3$; 123.59, C5; 143.91, C8; 149.53, C6; 154.59, C4; 159.87, C2.

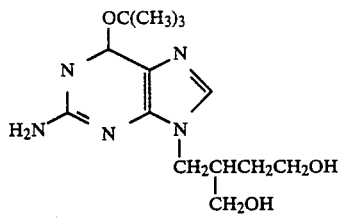

DEPROTECTION

A solution of crude 2-amino-6-tert.butoxy-9-[4-hydroxy-2-(hydroxy-2-(hydroxymethyl)butyl]purine (436 mg, 1.41 mmol) in 6 ml of 50% aqueous formic acid was kept at 100° C. for 3 h and then evaporated to dryness in vacuum, more water was added and the mixture was lyophilized. The residue was kept at 100° C. for 2 h with 10 ml of 2M aqueous ammonia. The ammonia was removed by a stream of nitrogen gas, the solution was heated to boiling, a small amount of solid matter was removed, and the filtrate was cooled in the refrigerator to afford 208 mg of crystalline 9-[4-hydroxy-2-(hydroxymethyl)butyl]guanine.

$^{13}$C NMR (DMSO-d$_6$): δ31.80, C$\underline{H}_2$CH$_2$OH; 38.17, CH; 44.35, NCH$_2$; 58.80 and 60.94, 2CH$_2$OH; 116.64, C5; 138.05, C8; 151.57, C4; 153.57, C2; 156.92, C6.

EXAMPLE 4

Preparation of 4-(2-Amino-1,6-dihydro-6-oxopurin-9-yl)-2-hydroxymethylbutyric acid (Method A)

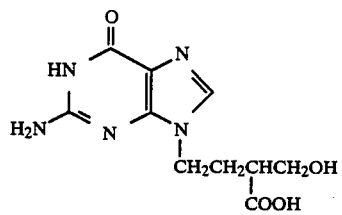

2-Amino-6-chloropurine (3.37 g, 19.9 mmol), 4-bromo-2-hydroxymethylbutyric acid ethyl ester (4.49 g, 19.9 mmol) and anhydrous potassium carbonate (2.75 g, 19.9 mmol) were mixed with 50 ml of dimethylformamide and the mixture was stirred at room temperature during 92 hours. The mixture was then filtered and the filtrate evaporated. The residue was extracted with 3×50 ml chloroform and the combined extracts were evaporated. Flash chromatography (silica gel, chloroform-methanol 10:1) and two recrystallizations from water afforded 0.995 g of the 4-(2-amino-6-chloropurin-9-yl)-2-hydroxymethylbutyric acid ethyl ester.

$^{13}$C NMR (CDCl$_3$): ppm 173.56, 159.40, 153.81, 151.16, 142.38, 124.89, 62.61, 61.11, 45.08, 41.91, 28.46 and 14.16.

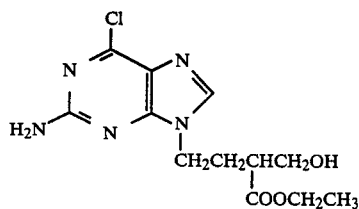

DEPROTECTION 4-(2-Amino-6-chloropurin-9-yl)-2-hydroxymethylbutyric acid ethyl ester (0.80 g) in 50 ml 1M hydrochloric acid was refluxed during 3 hours and then evaporated in vacuum, re-evaporated with 3×10 ml of water and the residue dissolved in 5 ml of water. The pH was then adjusted to 6-7 with solid sodiumbicarbonate. The solution obtained was filtered and the pH was adjusted to 4 with acetic acid. After cooling to 0° C. the precipitate was filtered off and washed with water. Recrystallization from water gave 0.43 g of 4-(2-amino-1,6-dihydro-6-oxopurin-9-yl)-2-hydroxymethylbutyric acid.

$^{13}$C NMR (DMSO-d$_6$): ppm 174.80 (C=O), 157.09 (C6), 153.64 (C2), 151.38 (C4), 137.49 (C8), 116.84 (C5), 62.15 (CH$_2$OH), 45.59 (CH), 41.33 (NCH$_2$) and 28.66 (N—CH$_2$—CH$_2$).

The starting compound, 4-bromo-2-hydroxymethylbutyric acid ethyl ester was prepared as follows:

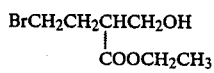

2-Hydroxymethylbutyrolactone [G. Claesson et al. Arkiv för kemi 28, 173 (1967)], (3.0 g) was dissolved in 20 ml ethanol and the solution was saturated with hydrogen bromide at 0° C. After standing at 0° C. during 0.5 hour, the solvent was evaporated at a low pressure. The residue was mixed with ice-water and the mixture neutralized with 10% aqueous sodium carbonate. The mixture was then extracted several times with diethyl ether and the combined ether extracts were washed with saturated, aqueous sodium chloride and dried over anhydrous sodium sulphate. After evaporation of the solvent, the residue was dissolved in 25 ml chloroform and filtered. Evaporation of the solvent yielded 4.59 g of the compound 4-bromo-2-hydroxymethylbutyric acid ethyl ether.

$^{13}$C NMR (CDCl$_3$): ppm 174.14, 62.54, 61.08, 46.02, 31.45, 38.89 and 14.26.

EXAMPLE 5

9-[4-Hydroxy-2-(hydroxymethyl)butyl]guanine hydrochloride

9-[4-Hydroxy-2-(hydroxymethyl)butyl]guanine (46 mg; Example 1) was dissolved in 0.4 ml of 1M aqueous hydrochloric acid and the solution was lyophilized (0.1 mm Hg) over-night. The residue (53 mg, quantitive yield) was dissolved in a few drops of warm ethanol and precipitated with several volumes of tetrahydrofuran to yield a white, crystalline product. M.p. ~85° C. (d).

$^1$H NMR (D$_2$O): δ1.61 (m, 2H) CH$_2$CH$_2$OH; 1.87 (m, 1H); 2.31 (septet, 1H) CH; 3.57 (d, 2H) CHCH$_2$OH; 3.72 (diffuse q) CH$_2$CH$_2$OH; 4.32 (m, 2H) NCH$_2$; 4.90 (s) HDO; 8.96 (s, 1H) H$_8$.

EXAMPLE 6

9-[4-Hydroxy-3-(hydroxymethyl)-2-butenyl]guanine (Method A)

VSA 668

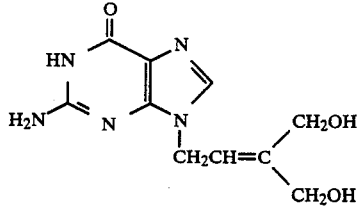

Crude 1-benzyloxy-2-benzyloxymethylbut-3-en-2-ol (1.42 g, 3.16 mmol) in 10 ml of CH$_2$Cl$_2$ was added to 0.71 g thionyl chloride (6 mmol) and 2 drops of DMF in 10 ml of CH$_2$Cl$_2$, and the solution was stirred for 0.5 h and evaporated in vacuum. Toluene was added and the mixture was evaporated in vacuum to yield crude 1-benzyloxy-2-benzyloxymethyl-4-chlorobut-2-ene.

A mixture of 1.61 g 2-amino-6-chloropurine (9.5 mmol) and 1.31 g finely ground anhydrous K$_2$CO$_3$ (9.5 mmol) in 50 ml of dry dimethylformamide (DMF) was kept at 100° C. for 5 min. and cooled. At 10° C. the crude 1-benzyloxy-2-benzyloxymethyl-4-chlorobut-2-ene in 25 ml of dry DMF was added with stirring during 4 h. After 2 days at room temperature the mixture was evaporated in vacuum, the residue was extracted with 2×25 ml of chloroform and the extract evaporated to dryness. Chromatography (silica gel, CHCl₃+MeOH 19+1) afforded 0.25 g (18%) of 4-(2-amino-6-chloropurin-9-yl)-1-benzyloxy-2-benzyloxymethyl-2-butene (TLC on silica gel, CHCl₃+MeOH 13+1 parts by volume Rf 0.62).

¹H NMR (CDCl₃-CD₃OD): δ4.05 and 4.19 (2s, 2×2H) =C(CH₂O)₂; 4.49 and 4.55 (2s, 2×2H) benzylic CH₂; 4.70 (d, 2H) N—CH₂; 5.85 (t, 1H) CH=; 6.2 (broad s, 2H) NH₂; 7.3 (broad s, 1OH) phenyl; 7.49 (s, 1H) H₈.

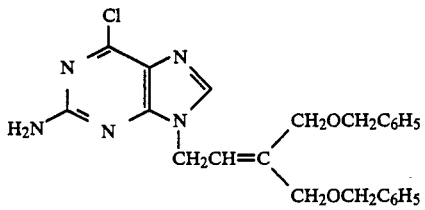

DEPROTECTION

A solution of 4-(2-amino-6-chloropurin-9-yl)-1-benzyloxy-2-benzyloxymethyl-2-butene (148 mg, 0.329 mmol), 1.8 ml of trifluoroacetic acid and 0.2 ml of water in a sealed ampoule was kept at 110° C. for 17 h. After cooling the mixture was diluted with 2 ml of water, heated to boiling for one minute, and evaporated to dryness in vacuum, dissolved in water and re-evaporated. Chromatography (silica gel, ethyl acetate+methanol+water 70+20+10 parts of volume) afforded 34 mg (41%) of 9-[4-hydroxy-3-(hydroxymethyl)-2-butenyl]guanine.

¹H NMR (DMSO-d₆): δ3.96 and 4.10 (2d, 2×2H) =C(CH₂O)₂; 4.68 (d, 2H) N—CH₂; 4.83 (2t, 2H) 2OH; 5.60 (t, 1H) CH=; 6.50 (broad s, 2H) NH₂; 7.66 (s, 1H) H₈; 10.6 (broad s, 1H) NH.

The starting compound 1-Benzyloxy-2-benzyloxymethylbut-3-en-2-ol, was prepared as follows:

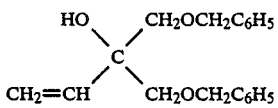

A solution of 4.0 g vinyl bromide (37.4 mmol) in 8 ml of dry tetrahydrofuran (THF) was added to 0.94 g Mg (38.7 mmol) in 3 ml of THF under N₂ at about 60° C. and the mixture was refluxed (CO₂—ethanol condenser) for 1 h.

A solution of 7.4 g (27.4 mmol) of 1,3-bis(benzyloxy)-propan-2-one (Araki Y. et al., J. Chem. Soc., Perkin Trans. 1, 1981, 19) in 25 ml of THF was added dropwise at 10° C. and the mixture was stirred at ambient temperature for 2 h. Then 8 ml of a 20% aqueous NH₄Cl solution was added, and the organic phase was evaporated, dissolved in ether, dried with MgSO₄, and evaporated in vacuum to give 7.90 g of 1-benzyloxy-2-benzyloxymethylbut-3-en-2-ol as a crude oil.

¹H NMR (CDCl₃): δ2.67 (s, 1H) OH; 3.50 (s, 4H) C(CH₂O)₂; 4.55 (s, 4H) 2OCH₂Ph; 5.0-6.3 (m, 3H) CH₂=CH; 7.32 (broad s, 1OH) phenyl.

EXAMPLE 7 cis-9-(4-Hydroxy-2-butenyl)guanine (Method B)

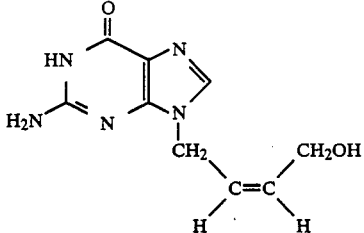

VSA 151

2-Amino-6-chloropurine (3.4 g), butadiene monoepoxide (1.65 g) and tetrakis (triphenylphosphine)palladium (0) (1.0 g) in dry dimethylformamide (75 ml) were stirred under a nitrogen atmosphere and heated at 60° C. for 45 minutes. The solvent was evaporated in vacuum (0.1 mm Mg) and the residue was triturated with hot chloroform (4×50 ml). The combined chloroform solutions were concentrated (25 ml volume) and diluted with ether (100 ml). The gummy precipitate was collected, dried and triturated with hot 1,2-dimethoxyethane (3×50 ml). The combined solutions were evaporated in vacuum (0.1 m Hg) to give a crude mixture (4 g) which was separated on a column of silica gel (500 g) eluted with chloroform+methanol 10+1 (800 ml) followed by chloroform+methanol 8+1. Fractions of about 15 ml were collected and the compound cis-4-(2-Amino-6-chloropurin-9-yl)-2-buten-1-ol was obtained as a minor product (0.2 g) in fractions 74–78. M.p. 160°–165° C.

UV spectrum, λ_max (nm): 0.1M HCl 241, 315; 0.1M NaOH 246, 308.

¹H NMR (DMSO-d₆): δ4.20 (t, J 5.4 Hz, 2H) CH₂O; 4.76 (d, J 6.8 Hz, 2H) NCH₂; 5.54–5.83 (m, 2H) CH=CH; 6.69 (s, 2H) NH₂; 8.06 (s, 1H) H₈.

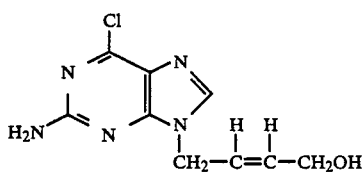

DEPROTECTION cis-4-(2-Amino-6-chloropurin-9-yl)-2-buten-1-ol (50 mg) in formic acid-water 7+3 (5 ml) was heated at 45° C. under a nitrogen atmosphere for 20 hours. The solvent was evaporated in vacuum and the residue was dried. Water (0.5 ml) was added and the solution was neutralized with aqueous ammonia. The precipitate was filtered, washed with water, ethanol and ether, and dried to give the compound cis-9-(4-hydroxy-2-butenyl)guanine (40 mg).

¹H NMR (DMSO-d₆): δ4.15 (diffuse t, 2H) CH₂O; 4.65–4.90 (ABX system, 2H) NCH₂; 5.75 (m, 2H) CH=CH; 6.52 (broad s, 2H) NH₂; 7.66 (s, 1H) H₈.

EXAMPLE 8

9-(4-hydroxy-2-butynyl)guanine (Method A)

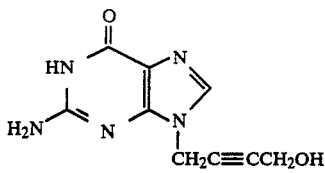

VSB 631

N-Bromosuccinimide (1.78 g, 10 mmol) was added in portions to a stirred suspension of 2-butyne-1,4-diol (2.50 g, 30 mmol) and triphenylphosphine (2.62 g, 10 mmol) in 20 ml of dichloromethane at room temperature. After 1 h, the unreacted butynediol was removed by filtration. The solution was evaporated in vacuum to small volume, dissolved in 20 ml of dry dimethylformamide (DMF) and added to a suspension of 2-amino-6-chloropurine (1.70 g, 10 mmol) and finely ground anhydrous $K_2CO_3$ (2.07 g, 15 mmol) in 75 ml of dry DMF, stirred at 0° C. The stirring was continued at room temperature for 3 days. Then the mixture was evaporated in vacuum to dryness. Chromatography (silica gel, $CHCl_3+MeOH$ 7+1) afforded 467 mg (20%; after recrystallization from water to remove 2-butyne-1,4-diol) of 4-(2-amino-6-chloropurin-9-yl)-2-butyn-1-ol (TLC on silica gel, $CHCl_3+MeOH$ 5+1; $R_f$ 0.57).

$^1H$ NMR (DMSO-$d_6$): δ4.10 (dt, 2H) $CH_2O$; 4.96 (t, J=2.0 Hz, 2H) $NCH_2$; 5.12 (t, J=5.9 Hz, 1H) OH; 6.89 (broad s, 2H) $NH_2$; 8.17 (s, 1H) $H_8$.

$^{13}C$ NMR (DMSO-$d_6$): δ32.79 ($NCH_2$); 49.07 ($CH_2O$); 77.80 and 85.19 (C≡C); 123.43 (C5); 142.43 (C8); 149.82 (C6); 153.69 (C4); 160.01 (C2).

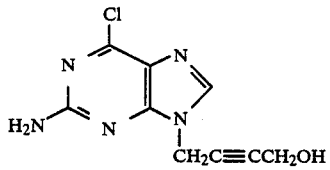

DEPROTECTION

A solution of 4-(2-amino-6-chloropurin-9-yl)-2-butyn-1-ol (140 mg, 0.59 mmol) in 2 ml of 50% aqueous formic acid was kept at 80° for 6 h and then evaporated to dryness in vacuum. The residue was dissolved in 2 ml of water—conc. aqueous ammonia 1+1 and the solution kept at 80° for 1 h and then evaporated in vacuum to dryness. Recrystallization from water afforded 90 mg (70%) of 9-(4-hydroxy-2-butynyl)guanine.

$^1H$ NMR (DMSO-$d_6$): δ4.09 (m, 2H) $CH_2O$; 4.84 (t, J=2.0 Hz, 2H) $NCH_2$; 5.11 (t, J=6.0 Hz, 1H) OH; 6.44 (broad s, 2H) $NH_2$; 7.73 (s, 1H) $H_8$.

The following examples illustrate the preparation of pharmaceutical compositions of the invention. The wording "active substance" denotes a compound according to the present invention or a salt thereof.

Tablets

Each tablet contains:

| | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 250.0 mg |

Suppositories

Each suppository contains:

| | |
|---|---|
| Active substance | 20.0 mg |
| Ascorbyl palmitate | 1.0 mg |
| Suppository base (Imhausen H or Witepsol ® H) | ad 2000.0 mg |

Syrup

| | |
|---|---|
| Active substance | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

Injection solution

| | |
|---|---|
| Active substance | 3.000 mg |
| Sodium pyrosulfite | 0.500 mg |
| Disodium edetate | 0.100 mg |
| Sodium chloride | 8.500 mg |
| Sterile water for injection | ad 1.00 ml |

Sublingual tablets

| | |
|---|---|
| Active substance | 5.0 mg |
| Lactose | 85.0 mg |
| Talc | 5.0 mg |
| Agar | 5.0 mg |
| | 100.0 mg |

Jelly

| | |
|---|---|
| Active substance | 1.0 g |
| Methocel ® | 4.0 g |
| Methyl p-hydroxybenzoate | 0.12 g |
| Propyl p-hydroxybenzoate | 0.05 g |
| Sodium hydroxide and hydrochloric acid to pH 6.7 | |
| Distilled water | ad 100.0 ml |

Ointment I

| | |
|---|---|
| Active substance | 1.0 g |
| Cetyltrimethylammoniumbromide | 0.6 g |
| Stearyl alcohol | 2.25 g |
| Cetanol | 6.75 g |
| Paraffin, liquid | 17.0 g |
| Glycerol | 12.0 g |
| Hydrochloric acid to pH 6.5 | |
| Distilled water | ad 100.0 g |

Ointment II

| | |
|---|---|
| Active substance | 3.0 g |
| Polyethylene glycol 1500 | 50 g |
| Polyethylene glycol 4000 | 15 g |
| Propylene glycol | ad 100 g |

Ointment III

| | |
|---|---|
| Active substance | 3.0 g |
| Sorbitan monoleate | 5.0 g |
| Petroleum | ad 100 g |

Ointment IV

| | |
|---|---|
| Active substance | 5 g |
| Adeps lanae | 20 g |
| Tween ® 60 | 4 g |
| Span ® 40 | 2 g |
| Paraffin, liquid | 4 g |
| Propylene glycol | 5 g |
| Hydrochloric acid to pH 6.5-8 | |
| Sterile water | ad 100 g |

Ointment V

| | |
|---|---|
| Active substance | 5 g |
| Adeps lanae | 20 g |
| Tween ® 60 | 4 g |
| Span ® 40 | 2 g |
| Paraffin, liquid | 4 g |
| Propylene glycol | 5 g |
| Boric acid | 2 g |

-continued

| | |
|---|---|
| Sodium hydroxide to pH 6.5-8 | |
| Sterile water | ad 100 g |
| Eye drops I | |
| Active substance | 0.1 g |
| Disodium edetate | 0.10 g |
| Sodium chloride for isotonia q.s. | |
| Hydrochloric acid to pH 6.5-8 | |
| Methocel ® 65 HG 4000 | 0.65 |
| Sterile water | ad 100 ml |
| Eye drops II | |
| Active substance | 0.3 g |
| Disodium edetate | 0.10 g |
| Sodium chloride for isotonia q.s. | |
| Hydrochloric acid to pH 6.5-8.0 | |
| Methocel ® 65 HG 4000 | 0.65 |
| Sterile water | ad 100 ml |
| Eye drops III | |
| Active substance | 0.2 g |
| Disodium edetate | 0.1 g |
| Sodium chloride for isotonia q.s. | |
| Boric acid | 0.1 g |
| Methocel ® HG 4000 | 0.65 g |
| Sterile water | ad 100 ml |
| Eye ointment I | |
| Active substance | 5 g |
| Paraffin oil | 19 g |
| Petrolatum | 76 g |
| Cream | |
| Active substance | 3.0 g |
| Arlaton ® | 4.0 g |
| Cetanol | 2.0 g |
| Stearic acid | 2.0 g |
| Paraffin oil | 2.0 g |
| Propylene glycol | 2.0 g |
| Glycerol | 1.5 g |
| Methyl p-hydroxybenzoate | 0.06 g |
| Propyl p-hydroxybenzoate | 0.03 g |
| Sodium hydroxide | 0.002 g |
| Hydrochloric acid 2M to pH 8.0 (water phase) | |
| Distilled water | to 100 g |
| Jelly | |
| Active substance | 3.0 g |
| Methocel ® | 2.45 g |
| Glycerol | 10.0 g |
| Tween ® | 0.10 g |
| Methyl p-hydroxybenzoate | 0.06 g |
| Propyl p-hydroxybenzoate | 0.03 g |
| Sodium hydroxide | 0.002 g |
| Hydrochloric acid 2M to pH 8.0 | |
| Distilled water | to 100 g |
| Tablets | |
| Each tablet contains: | |
| Active substance | 100.0 mg |
| Starch | 60.0 mg |
| Lactose | 190.0 mg |
| Polyvinylpyrrolidone | 5.0 mg |
| Magnesium stearate | 5.0 mg |
| | 360.0 mg |

BIOLOGICAL TESTS

The inhibiting effect of compounds of the invention on herpesvirus was tested using the methods described below. The cellular toxicity of the compounds on host cell functions was also tested.

In the following the compound 9-[4-hydroxy-2-(hydroxymethyl)butyl]guanine (base) is denoted VSA 671, the compound 9-[4-hydroxy-3-(hydroxymethyl)butyl]guanine (base) is denoted VIS 873, the compound cis-9-(4-hydroxy-2-butenyl)guanine (base) is denoted VSA 151 and the compound 9-[4-hydroxy-3-(hydroxymethyl)-2-butenyl]guanine (base) is denoted VSA 668, Herpes simplex type 1 virus is denoted HSV-1, Herpes simplex type 2 virus is denoted HSV-2 and Varicella zoster virus is denoted VZV.

I. Inhibition of virus multiplication in cell cultures

The inhibition of HSV-1 (strain C42) by VSA 671, VIS 873, VSA 151 and VSA 668 has been measured in a plaque reduction assay in Vero (Green Monkey Kidney) cells and in HEL (human embryonic lung) cells as described by Ejercito et al., J. Gen. Virol. 2 357 (1968). The effect on VZV (several strains) multiplication in HL (human lung fibroblast) cells by VSA 671 was determined by measuring the formation of late antigens by the ELISA technique as described by B. Wahren et al., J. Virological Methods 6, 141-149 (1983). The results are shown in Table 1.

TABLE 1

Inhibition of herpesvirus multiplication by VSA 671, VIS 873, VSA 151 and VSA 668.

| | HSV-1 | | VZV |
|---|---|---|---|
| | in Vero cells | in HEL cells | in HL cells |
| Compound | Inhibition (%)/Conc. ($\mu M$) | $ID_{50}$ ($\mu M$) | $ID_{50}$ ($\mu M$) |
| VSA 671 | >90/1 | 0.2 | 1.3-2.5 |
| VIS 873 | >90/1 | 0.4 | |
| VSA 151 | >90/10 | 0.6 | |
| VSA 668 | >90/25 | | |

II. Affinity of VSA 671, VIS 873, VSA 151 and VSA 668 for herpesvirus-induced thymidine kinase Inhibition constants ($K_i$) showing the affinity for HSV-1 thymidine kinase was determined according to the method of A. Larsson et al., Antimicrob. Agents Chemother. 23, 664 (1983). The inhibition constants are shown in Table 2.

TABLE 2

Inhibition constants of VSA 671, VIS 873, VSA 151 and VSA 668 for HSV-1 thymidine kinase.

| Compound | $K_i$ ($\mu M$) |
|---|---|
| VSA 671 | 0.6 |
| VIS 873 | 1.5 |
| VSA 151 | 7 |
| VSA 668 | 25 |

A high affinity for the viral thymidine kinase is an advantage for antiviral activity under conditions when the compounds have to compete with thymidine. VSA 671 has an affinity close to that of the natural substrate, thymidine ($K_m$ 0.42 $\mu M$).

III. Cellular toxicity

VSA 671, VIS 873, VSA 151 and VSA 668 were tested for cellular toxicity on human embryonic cells as described by K. Stenberg [Biochemical Pharmacology 30, 1005-1008 (1980)]. All compounds showed low cellular toxicity (Table 3) at concentrations that inhibit herpesvirus multiplication to more than 90% (see Table 1).

TABLE 3

Cellular toxicity of VSA 671, VIS 873, VSA 151 and VSA 668, expressed as percent reduction in cell growth (Flow 1000) after 48 h of incubation.

| Conc. (μM) | Compound | Percent reduction in cell growth |
|---|---|---|
| 200 | VSA 671 | 18 |
| 200 | VIS 873 | 7 |
| 200 | VSA 151 | 0 |
| 200 | VSA 668 | 0 |

IV. Animal experiments (a) Experiments on cutaneous herpesvirus infection on guinea pigs were carried out as previously described by S. Alenius and B. Öberg [Archives of Virology 58, 277–288 (1978)]. The experiments showed that VIS 873 had a therapeutic effect on cutaneous herpesvirus infections when applied topically as shown in Table 4. Thirty μl of solution or solvent was added topically 3 times per day for 4 days starting 24 h post inoculation.

TABLE 4

Therapeutic effect on cutaneous herpesvirus infection

| Conc. of VIS 873 in dimethylsulfoxide % | Percent reduction in cumulative score as compared to placebo treatment |
|---|---|
| 2.5 | 36 |

(b) Treatment of a "systemic" HSV-1 or HSV-2 infection in mice with VSA 672 or VIS 873 i.p. was carried out as described in A. Larsson et al., Antimicrob. Agents Chemother. 23, 664–670 (1983).

Mice were infected with $10^5$ pfu (plague-forming units) HSV-1 (C42) or $10^4$ pfu HSV-2 (strain 91075) i.p., and treatment was started 1 h after infection. Treatment consisted of two daily i.p. doses of either nucleoside analog, dissolved in phosphate-buffered saline, for 5 days. Cumulative mortality (treated vs. untreated animals) was determined during the course of the experiment, i.e. 21 days. The results are shown in Table 5.

TABLE 5

Antiviral effect of VIS 873 and VSA 671 on systemic (i.p.) HSV-1 and HSV-2 infections in mice.

| Compound | Dose | Virus | Cumulative mortality (%) (treated/untreated) |
|---|---|---|---|
| VSA 671 | 25 mg/kg | HSV-1 | 30/90 |
| | 50 mg/kg | " | 30/90 |
| | 25 mg/kg | HSV-2 | 40/90 |
| | 50 mg/kg | " | 30/90 |
| VIS 873 | 5 mg/kg | HSV-1 | 30/80 |
| | 10 mg/kg | " | 0/80 |
| | 5 mg/kg | HSV-2 | 70/90 |
| | 10 mg/kg | " | 20/90 |
| | 25 mg/kg | " | 0/90 |
| | 50 mg/kg | " | 10/100 |

BEST MODE OF CARRYING OUT THE INVENTION

Among the compounds of the present invention according to formula I, the compounds 9-[4-hydroxy-3-(hydroxymethyl)butyl]guanine, 9-[4-hydroxy-(2-hydroxymethyl)butyl]guanine and cis-9-(4-hydroxy-2-butenyl)guanine and their use for the treatment of herpesvirus infections represent the best mode known at present. The compound 9-[4-hydroxy-2-hydroxymethyl)butyl]guanine has shown a very good effect against varicella zoster virus multiplication.

We claim:

1. A compound having the formula 9-[4-hydroxy-2-(hydroxymethyl)butyl]guanine or a physiologically acceptable salt or an optical thereof.

2. A antiviral preparation comprising as an active ingredient the compound of claim 1 together with a pharmaceutically acceptable carrier, the proportion of said carrier being such that the pharmaceutical preparation is effective to treat virus infections in an animal or human host in need of such treatment upon administration of the pharmaceutical preparation.

3. A method of treatment of virus infections in an animal or human host in need of treatment, comprising administering to the host a therapeutically effective amount of the compound of claim 1.

* * * * *

UNITED STATES PATENT AND TRADEMARK OFFICE
CERTIFICATE OF CORRECTION

PATENT NO. : 4,798,833
DATED : Jan. 17, 1989

Page 1 of 3

INVENTOR(S) : Johansson et al

It is certified that error appears in the above-identified patent and that said Letters Patent is hereby corrected as shown below:

Col. 1, line 9, change "deviations" to --derivatives--,
Col. 1, line 15, change "such" to --Such--,
Col. 1, line 26, change "other" to --others--,
Col. 1, line 51, change "carbinomas" to --carcinomas--,
Col. 1, line 55, change "tumorgenic" to --tumorogenic--.

Col. 2, line 63, Change "It has not" to --It has now--,
Col. 2, line 65, change "vunctions" to --functions--.

Col. 7, line 57, change "fluorinted" to --fluorinated--,
Col. 7, line 61, change "vareity" to --variety--,
Col. 7, line 62, change "protective" to --Protective--.

Col. 9, line 19, change "ad" to --as--,
Col. 9, line 21, change "100 C." to --100°C.--.

Col. 11, line 3 (first line of the formula), change "$R_{19}$" to --$R_{19a}$--.

Col. 12, line 51, change "functiional" to --functional--.

Col. 13, line 26, change "palladium (O)" to --palladium(0)-- (a zero not an O),
Col. 13, line 52, change "$R^{7b}$" to --$R_{7b}$--.

Col. 15, line 41, change "the purine" to --a purine--.

Col. 16, line 11, change "method" to --methods--.

Col. 17, line 52, change "dissoled" to --dissolved--.

UNITED STATES PATENT AND TRADEMARK OFFICE
CERTIFICATE OF CORRECTION

PATENT NO. : 4,798,833
DATED : Jan. 17, 1989
INVENTOR(S) : Johansson et al

It is certified that error appears in the above-identified patent and that said Letters Patent is hereby corrected as shown below:

Col. 18, line 40, change "stearyl alchol" to --stearyl alcohol--,
Col. 18, lines 40-41, change "polypropylen" to --polypropylene--,
Col. 18, line 61, change "of" to --or--.

Col. 19, line 63, change "CH$_2$CH$_2$OH" to --C$\underline{H}$$_2$CH$_2$OH-- (underline the first "H"),
Col. 19, line 64, change "CHCH$_2$OH" to --CHC$\underline{H}$$_2$OH-- (underline the second "H"),
Col. 19, line 65, change "CH$_2$CH$_2$OH" to --CH$_2$C$\underline{H}$$_2$OH-- (underline the second "H").

Col. 20, line 32, after "(CDCl$_3$)" insert --:-- (a colon),
Col. 20, line 34, change "(2s, 2 X H)" to --(2s, 2 X 3H)--.

Col. 22, line 64, change "CHCH$_2$CH" to --CHC$\underline{H}$$_2$CH-- (underline the second "H").

Col. 24, line 40, delete the formula in its entirety and substitute the following formula therefor:

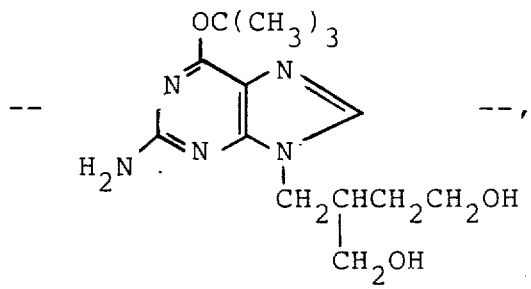

UNITED STATES PATENT AND TRADEMARK OFFICE
CERTIFICATE OF CORRECTION

PATENT NO. : 4,798,833

DATED : Jan. 17, 1989

INVENTOR(S) : Johansson et al

Page 3 of 3

It is certified that error appears in the above-identified patent and that said Letters Patent is hereby corrected as shown below:

Col. 24, line 53, delete "-2-(hydroxy" (first occurrence).

Col. 25, line 51, change "sodiumbicarbonate" to --sodium biocarbonate--.

Col. 26, line 33, change "$CH_2CH_2OH$" to --$\underline{C}H_2CH_2OH$-- (underline the first "H"), Col. 26, line 34, change "$CHCH_2OH$" to --$CH\underline{C}H_2OH$-- (underline the second "H"), Col. 26, line 35, change "$CH_2CH_2OH$" to --$CH_2C\underline{H}_2OH$-- (underline the second "H").

Col. 27, line 41, after "compound" insert --,-- (a comma).

Col. 28, line 29, change "0.1 m" to --0.1 mm--.

Col. 33, line 34, change "672" to --671--,
Col. 33, line 37, change "plague-forming" to --plaque-forming--.

Col. 34, line 32, (Claim 1), after "optical" insert --isomer--.

Signed and Sealed this

Twenty-fourth Day of December, 1991

*Attest:*

HARRY F. MANBECK, JR.

*Attesting Officer*   *Commissioner of Patents and Trademarks*